United States Patent [19]
Müller et al.

[11] Patent Number: 5,802,248
[45] Date of Patent: Sep. 1, 1998

[54] MULTI-SPEED MOTOR

[75] Inventors: Gregory C. Müller, Midland, Mich.; Lawrence M. Sears, Hunting Valley, Ohio

[73] Assignee: Tannas Co., Midland, Mich.

[21] Appl. No.: 582,211

[22] Filed: Jan. 2, 1996

[51] Int. Cl.$^6$ ............................................. H02P 1/18
[52] U.S. Cl. ........................ 388/822; 388/819; 318/772
[58] Field of Search ............................ 318/254, 138, 318/721, 798, 800, 727, 723, 719, 772, 773; 388/811, 815, 822, 819

[56] References Cited

U.S. PATENT DOCUMENTS

| | | | |
|---|---|---|---|
| 3,648,798 | 3/1972 | Jania | 180/105 E |
| 4,070,606 | 1/1978 | Morozumi et al. | 318/254 |
| 4,445,365 | 5/1984 | Selby | 73/60 |
| 5,367,234 | 11/1994 | DiTucci | 318/254 |
| 5,389,862 | 2/1995 | Tominaga | 318/254 |
| 5,414,331 | 5/1995 | Izawa et al. | 318/254 |
| 5,565,621 | 10/1996 | Selby et al. | 73/54.28 |

*Primary Examiner*—John W. Cabeca
*Attorney, Agent, or Firm*—Christopher John Rudy

[57] ABSTRACT

Control circuitry for a multi-speed, rotational, direct current motor can include a means to select one of a plurality of discrete circuits to select a desired speed of the motor, each circuit being activated by a separate analog switch which can complete the circuit to select a potentiometer voltage which then becomes a speed reference voltage output; a motor encoder which generates a pulse train proportional to motor speed and is converted to a proportional voltage by means of a frequency-to-voltage converter; an error amplifier, connected to the outputs of the speed reference voltage and the motor speed voltage such that when the speed reference voltage differs from the motor speed voltage, an error signal is produced; a pulse width modifier circuit which is driven by the error signal and which adjusts motor logic outputs so as to adjust the speed of the motor to produce an essentially zero error; a power supply circuit to feed voltage to the controlling circuitry and motor. Optional reset and start-up circuits can initialize various circuit time constants so as to produce a controlled ramp upon start-up of the motor, especially for applications to dynamometry such as with rotational viscometers. The motor with such circuitry and/or components is provided as well.

10 Claims, 6 Drawing Sheets

MULTI-SPEED MOTOR

FIELD

The present invention concerns a multi-speed electric motor and its controlling circuitry, useful in providing controlled motive power, especially for a tapered bearing simulator rotational viscometer.

BACKGROUND

An electric motor is the driving element in a sensitive rotating viscometer such as the tapered bearing simulator viscometers invented and disclosed by Mr. Theodore W. Selby in U.S. Pat. No. 4,445,365 (May 1, 1984) and by Messrs. Selby and Gregory C. Miiller in U.S. Pat. No. 5,565,621 (Oct. 15, 1996) and sold by the Tannas Co., Midland, Mich. However effective such instruments are in determining viscosity, and they are the world's standards in that regard, the measurement of the viscosity of the fluid tested is currently done most frequently at generally one rotating speed, even though, originally, the TBS Tapered Bearing Simulator viscometer was designed with two speeds. At the lower of the two speeds, the motor occasionally vibrated. However, because of the fact that the motors are both hysteresis synchronous types, and thus dependent upon the electric power supply frequency, even the higher speed on the original motor and the motor with one speed may be subject to some fluctuation which can cause the measurement of viscosity to be less accurate than desired. A more full profile of the fluid viscosity at different shear rates would be desirable as well. It is known that the readout of viscosity in such a rotating viscometer is dependent on the motor speed which is proportional to the shear rate at which the measurement is taken.

SUMMARY

After a long and dedicated period of research, in which various ways and means were developed and tested to provide an accurate, precise, and variable speed electric motor especially suitable for driving a multi-speed tapered bearing simulator viscometer, which met with little if any effective success, the present invention was made. Provided thus is control circuitry for a multi-speed, rotational, direct current motor comprising a means to select one of a plurality of discrete circuits to select a desired speed of the motor, each circuit being activated by a separate analog switch which can complete the circuit to select a potentiometer voltage which then becomes a speed reference voltage output; a motor encoder system which generates a motor speed voltage output proportional to the motor speed; a circuit such as a comparator or error amplifier circuit, connected to the outputs of the speed reference voltage and the motor speed voltage such that when the speed reference voltage differs from the motor speed voltage, an error signal is produced; a pulse width modifier circuit which is driven by the error signal and which adjusts motor logic outputs so as to adjust the preselected speed of the motor to an essentially zero error; a power supply circuit to feed voltage to the controlling circuitry and motor. Optional reset and start-up circuits can initialize various circuit time constants so as to produce a controlled ramp upon start-up of the motor, especially for applications to dynamometry such as with rotational viscometers. Also provided are a speed-controllable, multi-speed, rotational, direct current motor and an instrument containing the same.

The invention is useful in controlling and providing controlled-rotation mechanical power from an electric power source. In particular, the multi-speed motor is employed well in a rotational viscometer or dynamometer, especially in a tapered bearing simulator device such as in the devices of the aforementioned documents of Selby and Selby et al.

Significantly, by the invention, a highly accurate, precise, rotating direct current electric motor is provided, which can have essentially zero error at any of a number of preselected motor speeds. For example, the motor speed accuracy can have a fluctuation of less than 0.1%, which is an essentially zero error. Standard parts may be employed, and the motor can be made efficiently.

Numerous further advantages attend the invention.

DRAWINGS

The drawings form part of the specification hereof. In the drawings, the following is briefly noted:

ILLUSTRATIVE DETAIL

The invention can be further understood by reference to the present detail and drawings, which are to be construed as illustrative and not necessarily limiting in nature.

The aforementioned patent documents are incorporated herein by reference.

Figure 1:
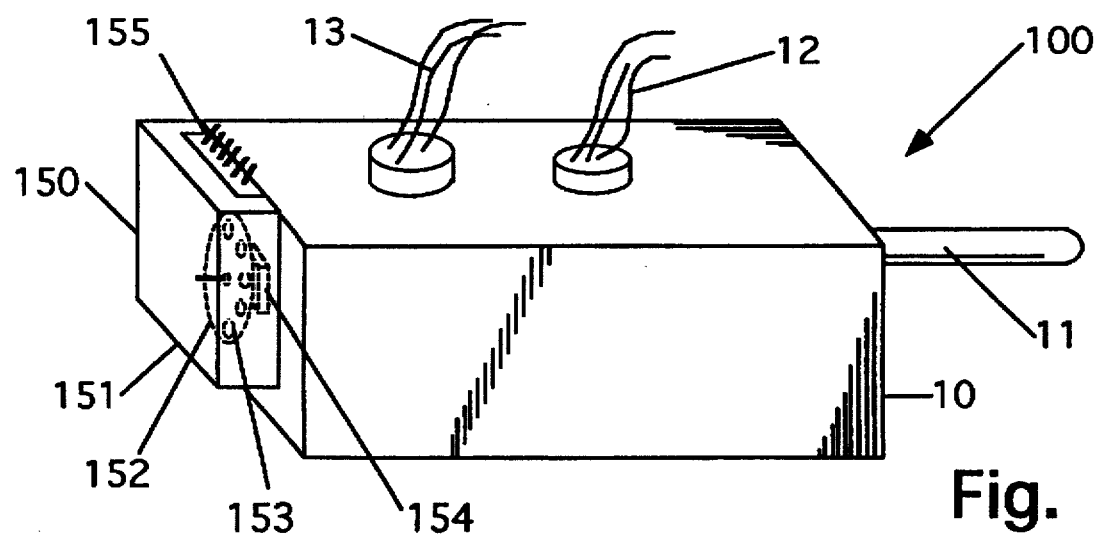
FIG. 1 is a perspective, partial cut-away view of a multi-speed motor of the invention, for a tapered bearing simulator viscometer as of the aforementioned documents of Selby and Selby et al., which employs the circuitry depicted in FIG. 3.

In reference to present FIG. 1, rotating shaft direct current (DC) motor 100, for example, a TELECOM (Reg. U.S. Pat. & Tm. Off.) PITTMANN (Reg. U.S. Pat. & Tm. Off.) brushless DC servomotor (No. 4261B618-R1, 22.3 mV/R/S, 0.70 Ohm, 5500-500, from Pittmann Division, Harleysville, Pa.) has motor housing 10, driving shaft 11, three power driver circuit wire connections 12, and five motor logic wire connections 13. Encoder 150, for example, a Hewlett Packard HEDS-5500 encoder (No. 5500-96 from Pittmann Division) is mounted directly to one end of the shaft 11 so as to be in a direct-drive (1:1) relationship therewith, although other ratios or proportions can be employed such as provided by gears, drive posts, pulleys, and so forth, connectable to the shaft 11 or by other means such as optical or electronic/magnetic sensing devices which monitor the shaft speed, and it includes encoder housing 151 mounted on the motor housing 10. An encoder 150 may contain a rotating disc 152 with encoding holes or marks 153, and means 154 for sensing or monitoring the rotating holes or marks 153 detects the rotating passage of the same. In any event, the encoder 150 generates signals proportional to the rotational speed of the motor shaft 11 and transmits them such as by means of connection pin wires 155. The motor 100 may be employed, for example, as the motor in the tapered bearing simulator devices of the aforementioned Selby and Selby et al. patent documents.

Figure 2:
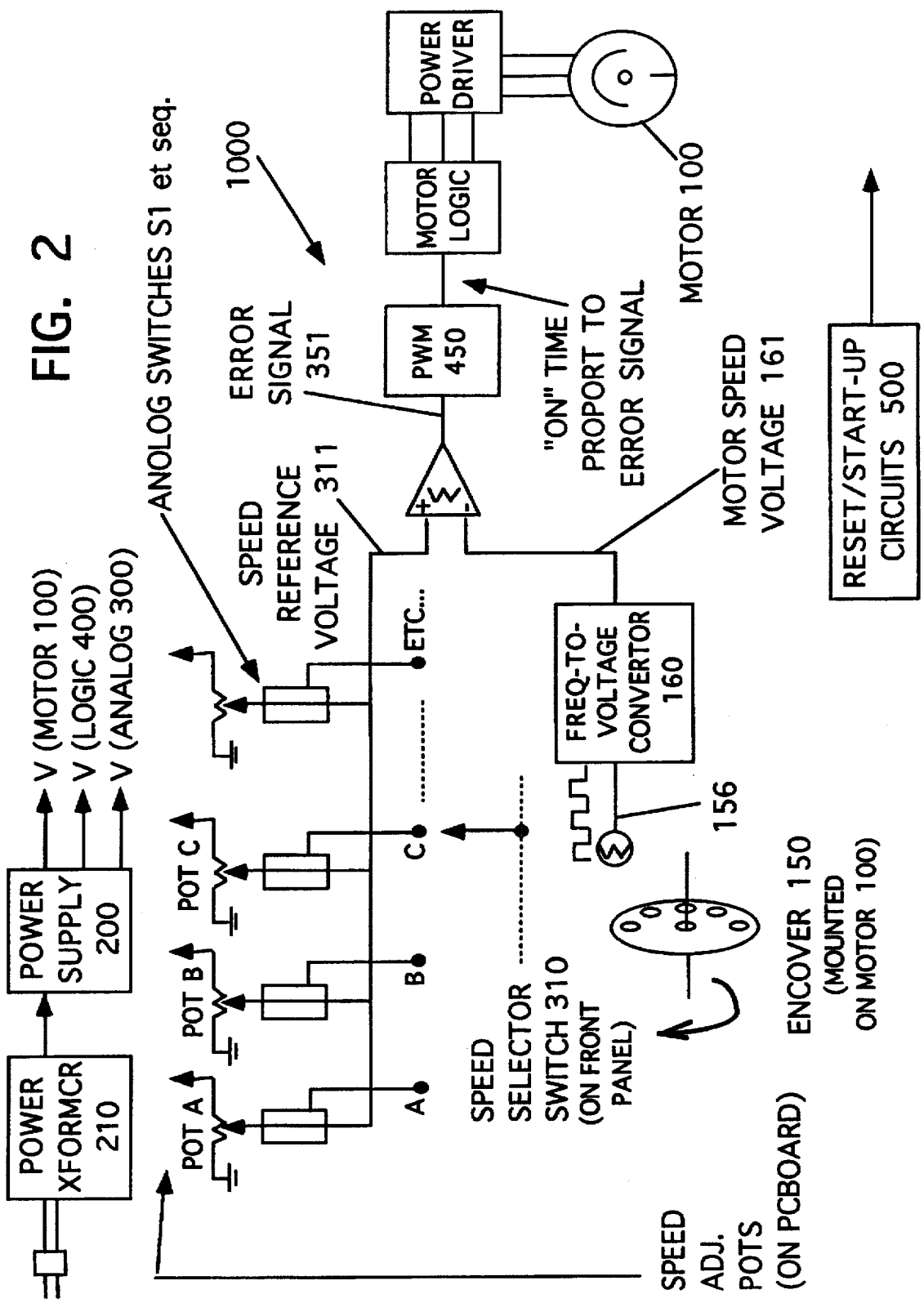
FIG. 2 is a general block diagram for multi-speed motor control circuitry hereof.
Figure 3:
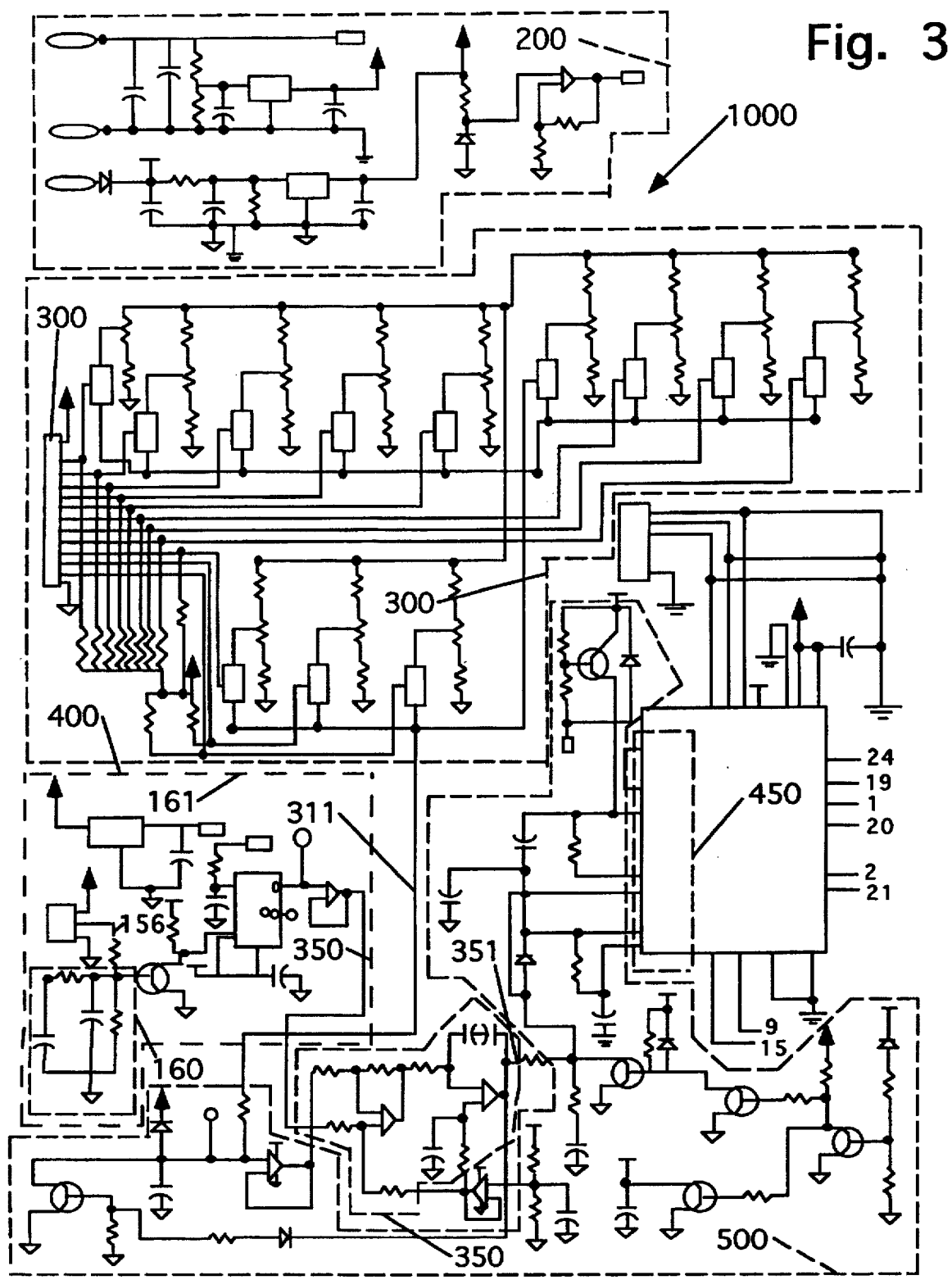
FIG. 3 is a particular circuit diagram for a multi-speed motor control circuit hereof.
Figure 3A:
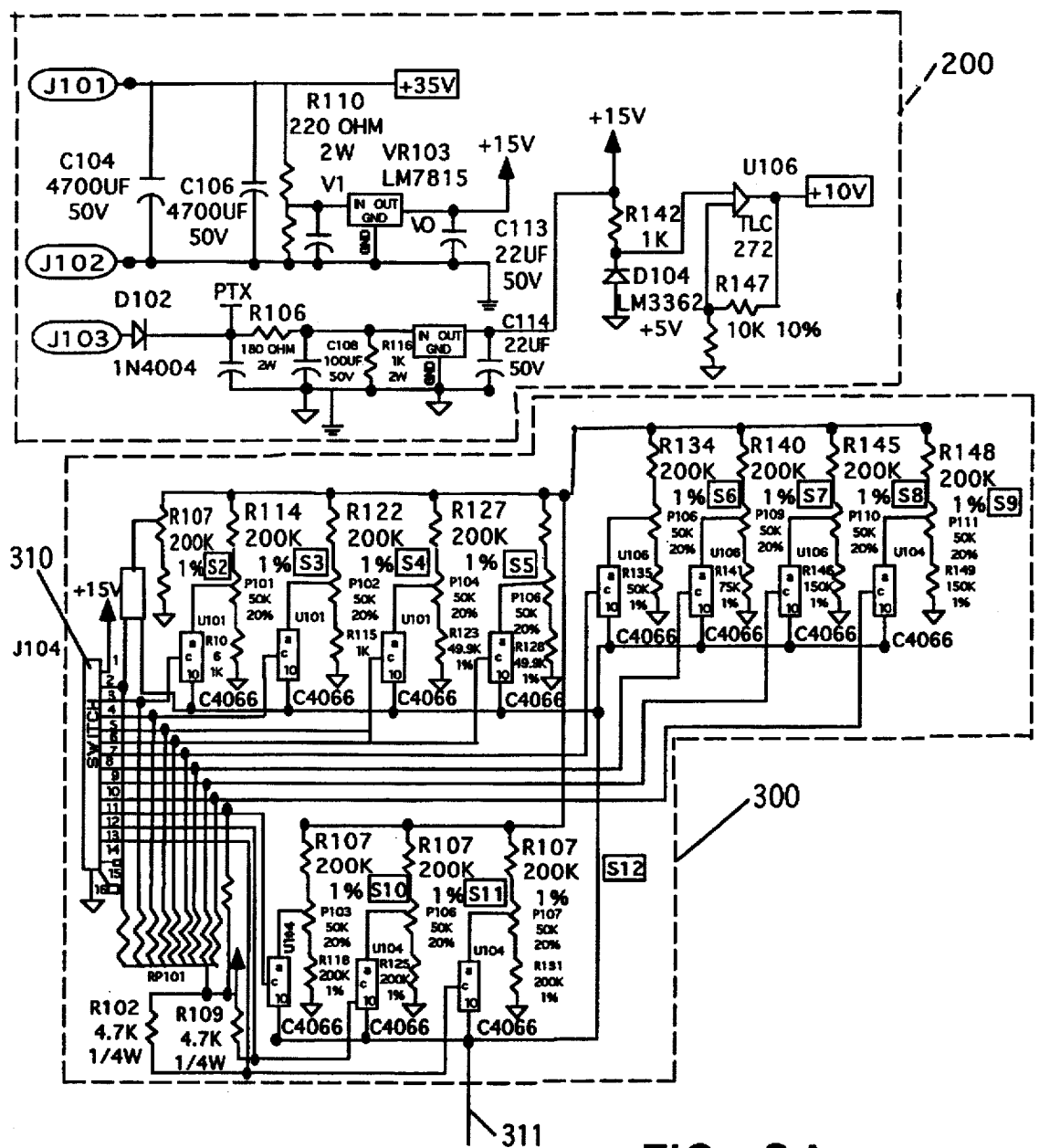
Figure 3B:
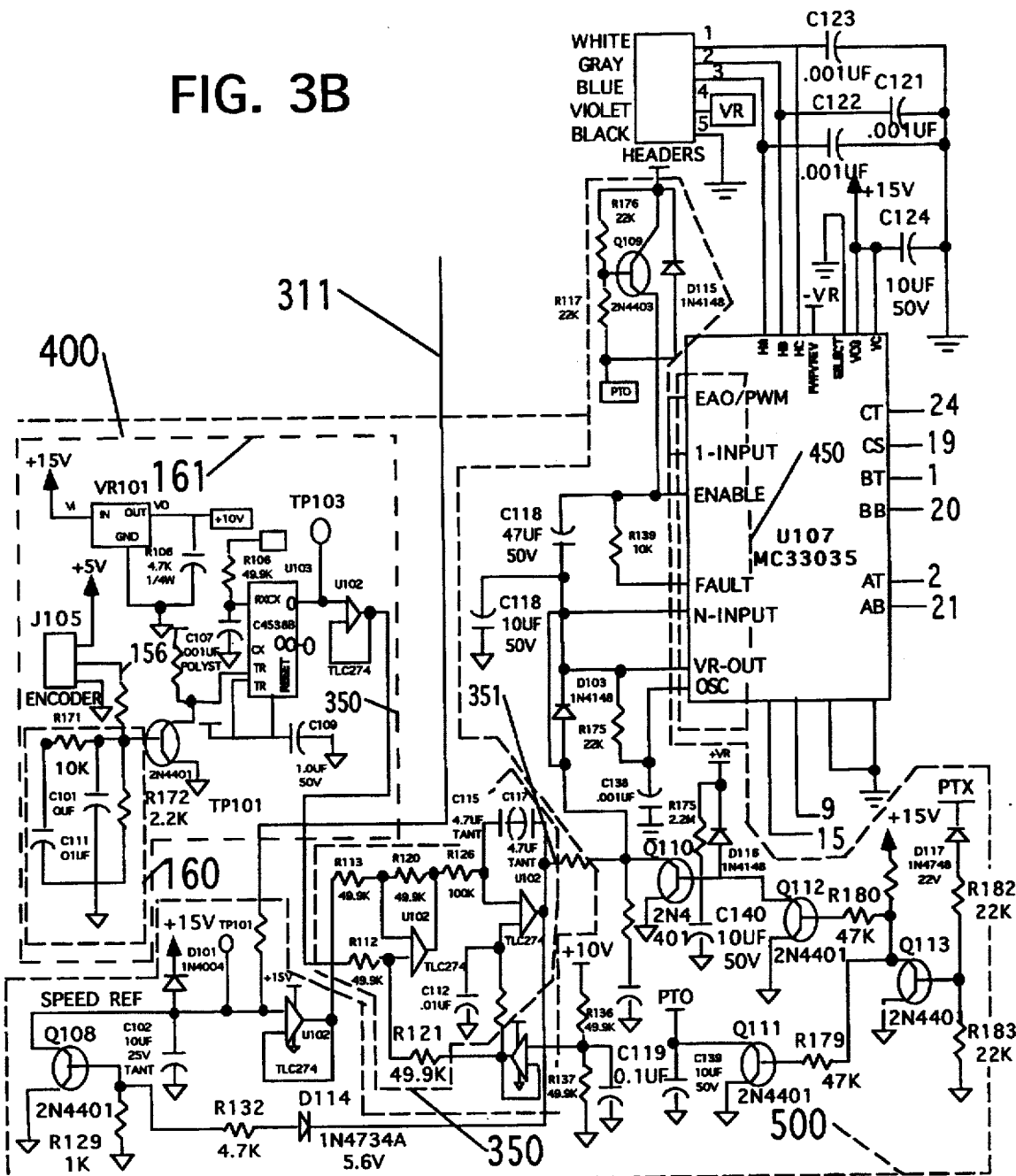
Figure 3C:
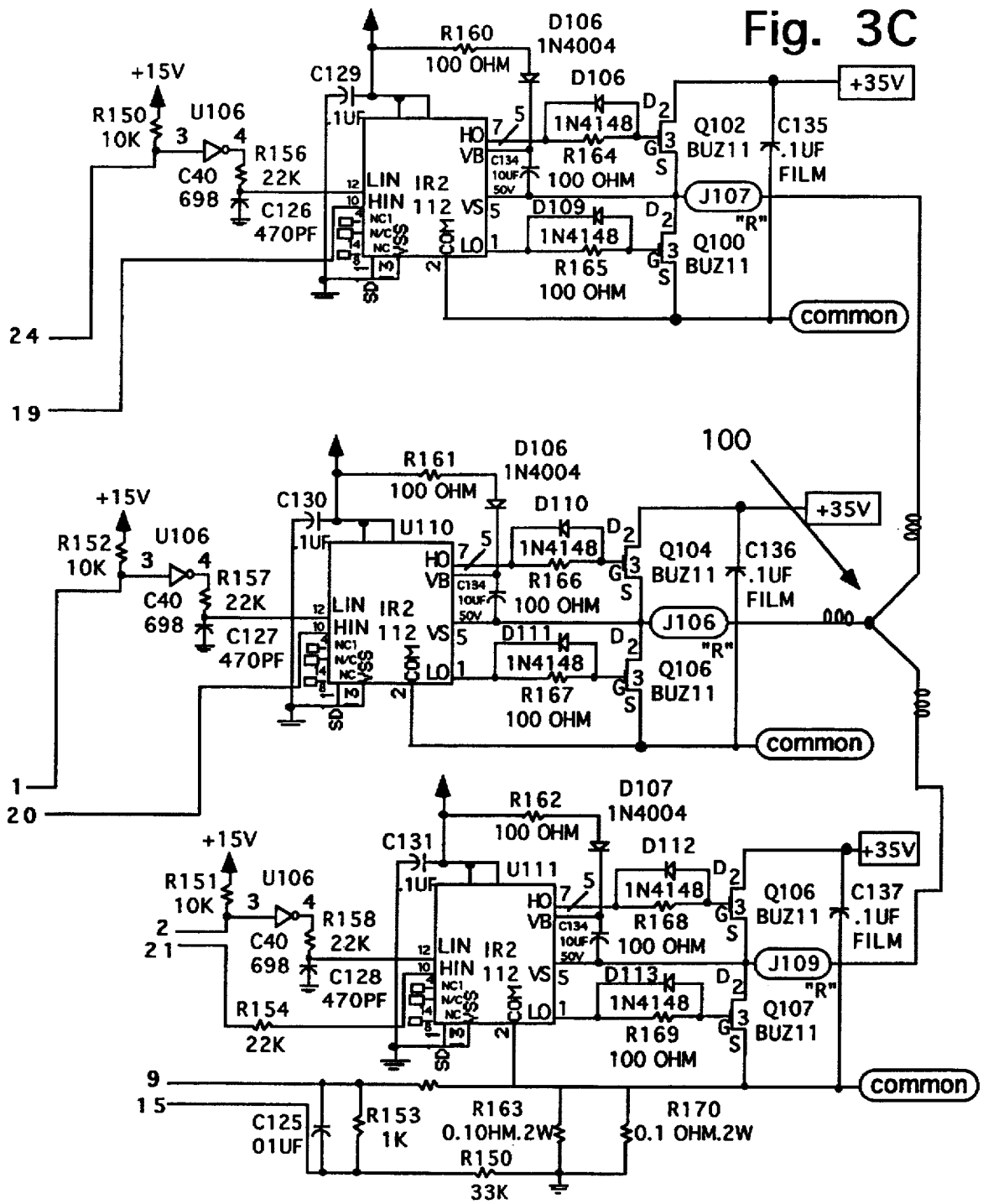

In reference to present FIGS. 2 & 3, control circuitry 1000, which may be mounted on a standard printed circuit (PC) board, has power supply circuitry 200 which can be connected to a power transformer 210 which can be connected to a power source such as a standard sixty-cycles per second alternating current (AC) source. The power supply 200 will supply power for the motor 100, for example, with thirty-five volts, and the controlling circuitry, to include analog circuitry 300, for example, with ten volts, and logic circuitry 400, for example, with fifteen volts. The PC board and its components can be housed in a console box. In conjunction with the analog circuitry 300, as the means to select one of a plurality of discrete circuits can be provided a standard switch 310, for example, to select and close one of twelve analog switches, S1, S2, S3, S4, S5, S6, S7, S8, S9, S10, S11 & S12. Each of these switches selects a different, desired operating speed for the motor 100, for example, an 800-rpm, 1500-rpm, 2000-rpm, 2500-rpm, 3000-rpm, 3500-rpm, 4000-rpm, 4500-rpm, 5000-rpm, 6000-rpm, 7000-rpm or 8000-rpm speed. Activation of each circuit by separate analog switches completes the appropriate circuit to select a potentiometer (pot) voltage. The selected pot voltage then becomes a speed reference voltage output 311. The motor encoder 150, for example, of the speed-to-pulse type, generates a pulse train output 156, which frequency is proportional to the speed of the motor, say, motor 100. The motor speed related output 156 is converted to a DC voltage via the frequency-to-voltage converter 160. Motor speed voltage output 161 results and feeds into error amplifier circuit 350. The speed reference voltage output 311 also feeds into the error amplifier circuit 350. The circuit 350 compares the two voltage outputs 161 & 311, and when they differ, an error signal output 351 is produced. Any error signal output is directed to pulse width modifier (PWM) circuit 450. The PWM circuit 450 is driven by the error signal output 351, and it adjusts motor logic outputs AT/AB, BT/BB & CT/CB so as to adjust the speed of the motor to produce an essentially zero error at 351. Reset and start-up circuits 500, which include transistors Q108, Q109, Q110, Q111, Q112 & Q113 and their surrounding components, are optional and can initialize various circuit time constants so as to produce a controlled ramp, i.e., a gradually increasing speed, for example, over an approximately five-second span, upon start-up of the motor until the operating speed of the motor is reached. This is especially useful for applications to dynamometry such as with rotational viscometers where sudden starting of the instrument motor, which drives a rotor in contact with a viscous test fluid, may cause undesirably sudden, high start-up torque levels which may cause breakage of a rotor shaft and consequent damage to the test cell. The gradual start-up generally avoids such undesirable effects.

CONCLUSION

The present invention is thus provided. Numerous modifications can be effected within its spirit, the literal claim scope of which is particularly pointed out as follows:

We claim:

1. Control circuitry for a multi-speed rotational motor comprising a means to select one of a plurality of discrete circuits to select a desired speed of the motor, each circuit being activated by a separate analog switch which can complete the circuit to select a potentiometer voltage which then becomes a speed reference voltage output; a motor encoder which generates a pulse train proportional to motor speed and is converted to a proportional voltage, called motor speed voltage, by means of a frequency-to-voltage converter; an error amplifier, connected to the outputs of the speed reference voltage and the motor speed voltage such that when the speed reference voltage differs from the motor speed voltage, an error signal is produced; a pulse width modifier circuit which is driven by the error signal and which adjusts motor logic outputs so as to adjust the speed of the motor to produce an essentially zero error; and a power supply circuit for feeding voltage to the control circuitry and motor.

2. The circuitry of claim 1, further comprising at least one of reset and start-up circuits which can initialize various circuit time constants so as to produce a controlled ramp upon start-up of the motor.

3. A speed-controllable, multi-speed, rotational, direct current motor comprising a direct current powered electric motor and control circuitry for the motor, said circuitry including a means to select one of a plurality of discrete circuits to select a desired speed of the motor, each circuit being activated by a separate analog switch which can complete the circuit to select a potentiometer voltage which then becomes a speed reference voltage output; a motor encoder which generates a pulse train proportional to motor speed and is converted to a proportional voltage, called motor speed voltage, by means of a frequency-to-voltage converter; an error amplifier, connected to the outputs of the speed reference voltage and the motor speed voltage such that when the speed reference voltage differs from the motor speed voltage, an error signal is produced; a pulse width modifier circuit which is driven by the error signal and which adjusts motor logic outputs so as to adjust the speed of the motor to produce an essentially zero error; and a power supply circuit for feeding voltage to the control circuitry and motor.

4. The speed-controllable, multi-speed, rotational, direct current motor of claim 3, wherein said circuitry further includes at least one of reset and start-up circuits which can initialize various circuit time constants so as to produce a controlled ramp upon start-up of the motor.

5. A rotational instrument comprising a motor and other instrument parts to make up the instrument, the motor being mounted in and forming a part of the instrument and being a speed-controllable, multi-speed, rotational, direct current motor having a direct current powered electric motor and control circuitry for the motor, said circuitry including a means to select one of a plurality of discrete circuits to select a desired speed of the motor, each circuit being activated by a separate analog switch which can complete the circuit to select a potentiometer voltage which then becomes a speed reference voltage output; a motor encoder which generates a pulse train proportional to motor speed and is converted to a proportional voltage, called motor speed voltage, by means of a frequency-to-voltage converter; an error amplifier, connected to the outputs of the speed reference voltage and the motor speed voltage such that when the speed reference voltage differs from the motor speed voltage, an error signal is produced; a pulse width modifier circuit which is driven by the error signal and which adjusts motor logic outputs so as to adjust the speed of the motor to produce an essentially zero error; and a power supply circuit for feeding voltage to the control circuitry and motor.

6. The instrument of claim 5, which is a dynamometer.

7. The rotational instrument of claim 5, wherein said circuitry further includes at least one of reset and start-up circuits which can initialize various circuit time constants so as to produce a controlled ramp upon start-up of the motor.

8. The instrument of claim 7, which is a dynamometer.

9. The instrument of claim 5, which is a viscometer.

10. The instrument of claim 6, which is a viscometer.

* * * * *